United States Patent [19]

Capriotti

[11] Patent Number: 4,938,234
[45] Date of Patent: Jul. 3, 1990

[54] METHOD OF SURGICALLY IMPLANTING A CONTOUR NASAL IMPLANT

[76] Inventor: Robert J. Capriotti, 2800 Garth Rd., Baytown, Tex. 77521

[21] Appl. No.: 219,983
[22] Filed: Jul. 15, 1988
[51] Int. Cl.$^5$ ............................................. A61B 19/00
[52] U.S. Cl. ...................................... 128/898; 623/10
[58] Field of Search ............... 128/303 R, 305, 897, 128/898; 623/10; 606/1

[56] References Cited

U.S. PATENT DOCUMENTS

| | | | |
|---|---|---|---|
| D. 263,747 | 4/1982 | Jaramillo et al. | D24/99 |
| D. 270,759 | 9/1982 | Straith | D24/3 |
| D. 286,910 | 11/1986 | Black | D24/33 |

FOREIGN PATENT DOCUMENTS 921536  4/1982  U.S.S.R. ................. 128/305

Primary Examiner—Randall L. Green
Assistant Examiner—Randy Shay
Attorney, Agent, or Firm—Vaden, Eickenroht, Thompson & Boulware

[57] ABSTRACT

A method is disclosed for surgically implanting a contour nasal implant into a nose of a patient to elevate the nasal tip and to augment and to improve the frontal and profile views of the patient's nose. The method comprises the steps of drawing, onto the nose of a patient into which a contour nasal implant is to be surgically implanted, a line connecting the highest points of the superior palpebral sulci such that the line crosses the nasal dorsum at a point representing the nasion and the highest point of implant insertion; placing two pledgets in each nostril in the nose of the patient; performing an open rhinoplasty incision into the skin located between the nostrils of the patient; retracting superiorly the columella skin off of the lower lateral cartilages on each side of the nostril up to the highest point of the natural dome of the nose of the patient; dissecting the skin off of the dorsum of the nose to the line previously drawn across the nasal dorsum; inserting a contour nasal implant having an elongated central member having a dorsal section, a predetermined shaped tip and a keel having a selected width and length which is located under the predetermined shaped tip with the keel thereof extending downward between the lower lateral cartilage until the desired implantation position is obtained; and suturing the rhinoplasty incision in the skin between the nostrils.

16 Claims, 3 Drawing Sheets

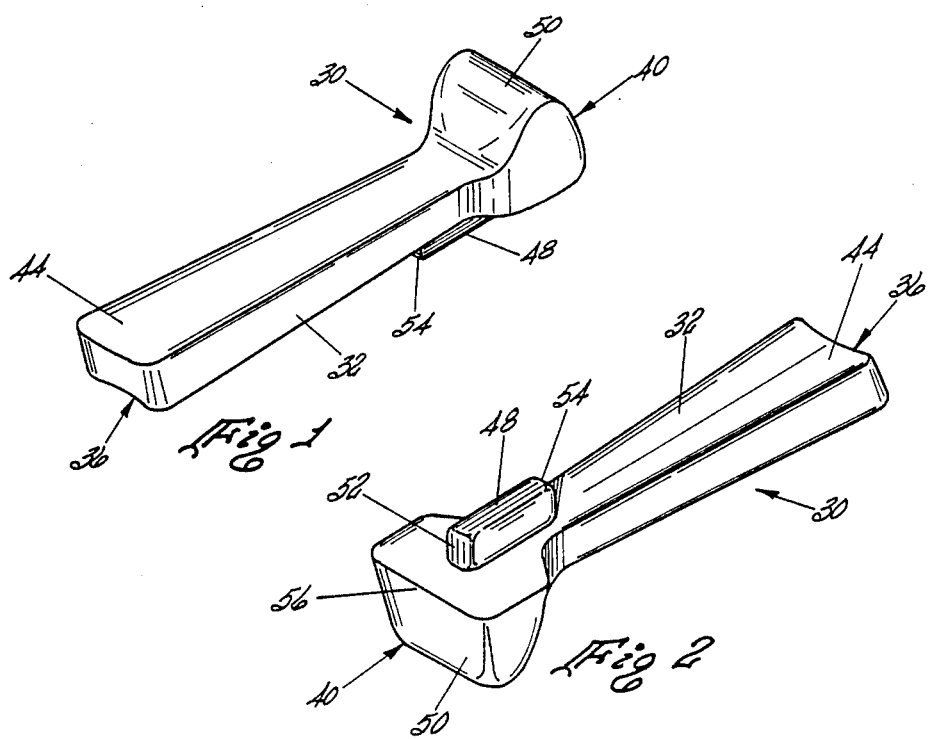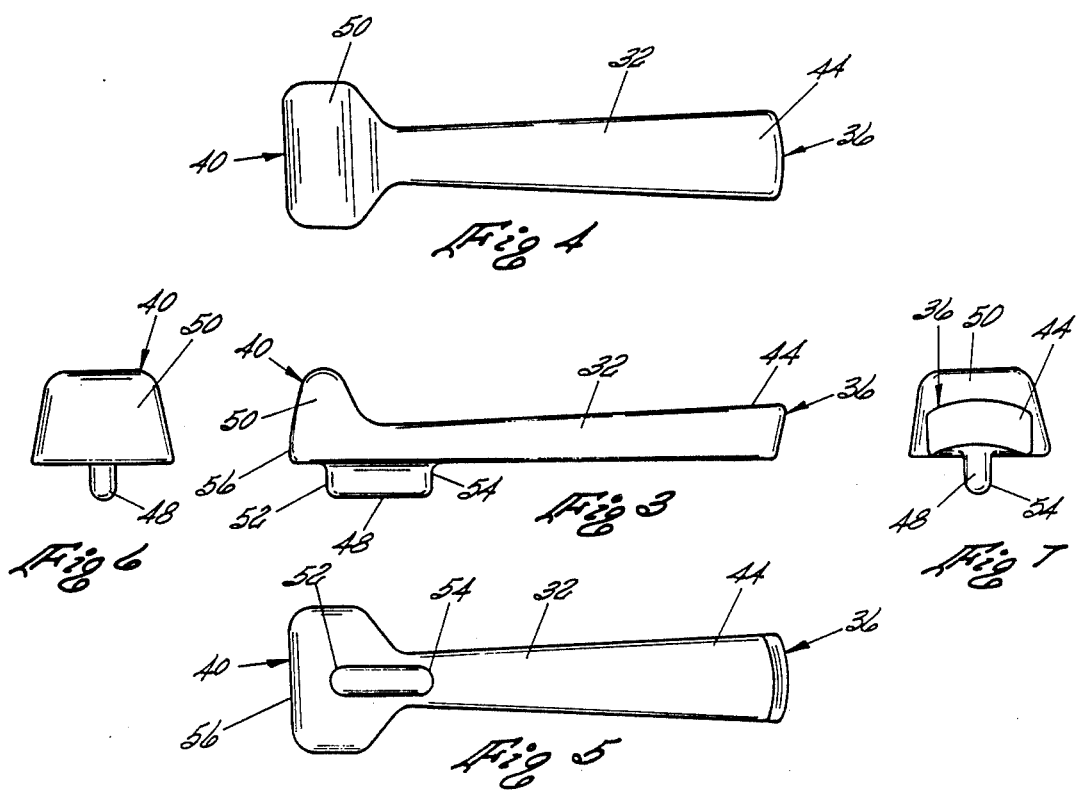

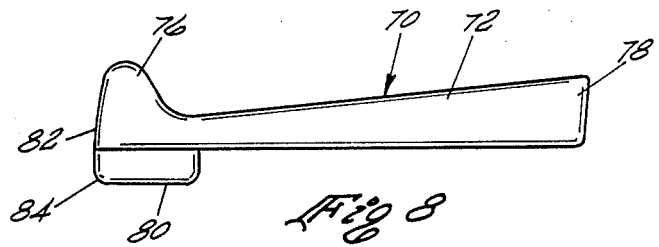
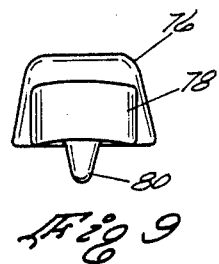
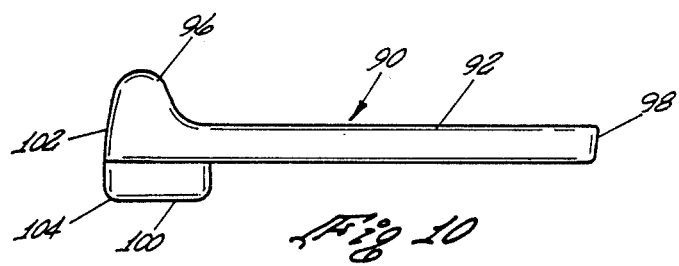
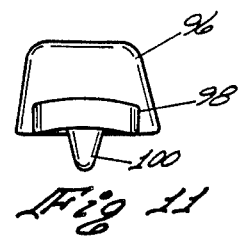
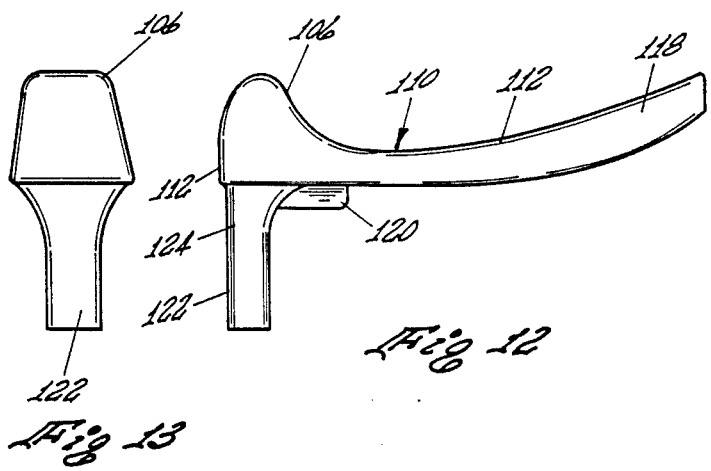
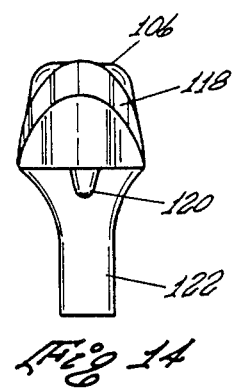

METHOD OF SURGICALLY IMPLANTING A CONTOUR NASAL IMPLANT

BACKGROUND OF THE INVENTION

1. Field of the Invention

This invention relates to a contour nasal implant used in the field of aesthetic nasal surgery or rhinoplasty for reshaping the nose to improve its appearance, and more specifically, relates to a contour nasal implant to be utilized in reconstructive surgery in non-caucasian rhinoplasty which requires augmentation of the nasal dorsum and elevation of the nasal tip. A method for surgically implanting the contour nasal implant is disclosed.

2. Description of the Prior Art

It is known in the art to perform plastic surgery to improve physical function or to overcome certain deficiencies in facial and body features such as disfigurement, scarring or the like, resulting from a variety of causes. Plastic surgery includes aesthetic surgery, sometimes known as cosmetic surgery, which has the specific purpose of reshaping or improving facial features or bodily figures. One popular form of plastic surgery is generally referred to as aesthetic nasal surgery or rhinoplasty, which can be defined as the reshaping of the nose to improve its appearance. It is well known in the plastic surgery field that aesthetic nasal surgery, or rhinoplasty, can involve a wide variety of surgical operations which may or may not include the use of nasal implants as a part thereof.

Typical examples of rhinoplasty surgery is where the patient has a large nose, nasal hump, and a large tip and a nose that hangs slightly where it meets the lips. In such situations, it is known in the art to gain access to the cartilage and bone within the nose and to cut and/or reshape the same to alter the exterior appearance of the nose.

Typically, a nasal hump is removed using either a sawing instrument, a chisel or rasp, leaving the ridge flat and with the bones and cartilage spread. Also, the bone structure can be manipulated to form a narrower nasal bridge. In certain situations, in order to reduce the size of the nasal tip, part of the cartilage and the lower lateral cartilages may be removed.

Also, it is known in the art to improve the angle between the nose and upper lip by elevating the nasal tip which is obtained by trimming the septum. A nasal implant may be used if required.

As the field of rhinoplasty has become more advanced, it has developed that certain individuals, particularly non-caucasians, require a special type of rhinoplasty which involves augmentation of the nasal dorsum and elevation of the nasal tip. As a result, it is a patient's desire that the final result look "natural", and this may require that the nasal tip be modified in accordance with the patient's desires.

It is known in the art to utilize a nasal implant which is formed of an elongated central member, a flared dorsal section and a septum strut. However, in performing non-caucasian rhinoplasty, the shape and physical characteristics of the known nasal implants do not provide the desired augmentation of the nasal dorsum and elevation of the nasal tip desired by the patient.

Thus, it is known in the art that, by utilizing the surgical procedure of an aesthetic rhinoplasty, that the overall size of the patient's nose can be modified or reduced, the nasal tip can be reshaped, a nasal hump can be removed or a poor angle between the nose and the upper lip can be improved. It is also known in the art that it is necessary to add tissue in order to improve the contour of the nose.

It is further known in the art that nasal surgery is performed under a local anesthetic which numbs the nasal area. However, in certain instances, a general anesthetic may be used. Medication is sometimes given to the patient before the anesthetic is administered in order to make the patient comfortable during the surgery.

The known surgical procedure for performing nasal surgery includes making an incision inside the nostrils. The nasal surgery is then performed through the incision, since the incision is sufficient to gain access to the lower lateral cartilage, the nasal bone including the nasal dorsum. It is also known in the art that the surgeon, by having access to the interior of the nose through the rhinoplasty incision, can cut, trim and manipulate the lower lateral cartilage or the bone to reshape the nose and alter its external appearance and to insert a nasal implant of the type known in the art.

DESCRIPTION OF THE INVENTION

The contour nasal implant of the present invention provides a unique, novel and improved contour nasal implant to be used in rhinoplasty surgery. The contour nasal implant of the present invention includes an elongated central member having a first end and a second end wherein the second end is spaced a predetermined distance from the first end. The first end is flared or somewhat concave in shape to define a dorsal support end which is adapted to be positioned over the nasal dorsum in the nose of a patient to augment the frontal and profile views of the nose. A second end includes a tip having a predetermined shaped which is located on the same side of the elongated central member as the dorsal support end. The second end further includes means for defining a keel having a selected width and length. The keel is located on the second end under the predetermined shaped tip and the keel is positioned substantially perpendicular to the elongated central member and positioned such that the length of the keel is generally parallel to the elongated central member. The predetermined shaped tip is operative to elevate the nasal tip of the nose of a patient into which the contour nasal implant is implanted and cooperates with the dorsal shaped end to contour the skin of the nose of the patient to define the desired frontal and profile views of the nose.

In addition, this invention discloses a novel and unique method for surgically implanting the contour nasal implant. Specifically, a method is disclosed for surgically implanting a contour nasal implant into a nose of a patient wherein the nose has lower lateral cartilages, a nasal dorsum and a nasal tip wherein the nasal dorsum and nasal tip are to be elevated and augmented to improve and reshape the frontal and profile views of the patient's nose. The method comprises the steps of drawing, onto the nose of a patient into which a contour nasal implant is to be surgically implanted, a line connecting the highest points of the superior palpebral sulci such that the line crosses the nasal dorsum at a point representing the nasion and the highest point of implant insertion; placing two pledgets in each nostril in the nose of the patient; performing an open rhinoplasty incision into the skin located between the nostrils of the patient; retracting superiorly the columella skin off of the lower lateral cartilages on each side of the nostril up to the highest point of the natural dome of the nose of the patient; dissecting the skin off of the dorsum of the nose to the line previously drawn across the nasal dorsum; inserting a contour nasal implant having an elongated central member having a first and a second end, wherein the first end thereof has a dorsal section which is adapted to be positioned over the nasal dorsum in the nose of a patient into which the same is to be implanted and wherein the second end includes a predetermined shaped tip located on the same side of the elongated central member as a dorsal section and further includes a keel having a selected width and length which is located under the predetermined shaped tip and wherein the keel has a length which is generally parallel to the elongated central member such that the first end thereof having a dorsal section is positioned between the nasal dorsum and the skin while the predetermined shaped tip portion thereof is located on the lower lateral cartilages and the keel thereof extends downward between the lower lateral cartilage until the desired implantation position is obtained; and suturing the rhinoplasty incision in the skin between the nostrils to implant the contour nasal implant within the nose of the patient to augment the frontal and profile views of the patient and to elevate the nasal tip of the nose of a patient.

As described hereinbefore in connection with the description of the prior art, aesthetic nasal surgery or rhinoplasty, is used to reshape the nose to improve its appearance. The type of rhinoplasty required depends upon the specific desires of the patient, the specific nose and cartilage structure of the patient and other factors such as the general characteristics of a nose identified with the heredity background of a patient. Certain ethnic groups exhibit nasal characteristics which include a concave nasal dorsum or an enlarged nasal tip resulting in the nose that hangs slightly where it meets the upper lip. In patients having such characteristics, the aesthetic rhinoplasty is performed to improve the frontal and profile views of the nasal dorsum and to reshape and/or elevate the nasal tip thereby improving the angle between the nose and the upper lip. In the known surgical procedures, it is typically necessary to add tissue in order to improve the contour of the nose.

Typically, patients can have the rhinoplasty performed using the known nasal implants and/or techniques for reshaping the nose. Such nasal implant utilized in rhinoplasty surgery utilizes a central member having a flared end which is positioned between the nasal dorsum and the skin to elevate the skin and utilizes a septum strut to cause elevation of the nasal tip.

Attempts have been made to utilize the known nasal implants in certain non-caucasian patients and these attempts have been less than acceptable. One reason is that the known nasal implants have certain deficiencies in that certain non-caucasian patients require that the nasal tip be significantly reshaped while concurrently elevating the nasal tip relative to the lip. The known nasal implants utilizing the septum strut do not provide sufficient material and/or structure to provide the desired amount of reshaping and elevation that is necessary to meet the patient's desires nor do the prior art nasal implants provide sufficient additional tissue material to significantly elevate and improve frontal and profile views of the nose. Also, the nasal implants are not anchored to the lower lateral cartilages of the nose with any anchoring means.

The present invention overcomes the inherent disadvantages associated with the prior art nasal implants for several important reasons.

One advantage of the present invention is that the contour nasal implant includes an elongated central body having a flared or concave end at one end thereof which defines a dorsal section and, which has at the other end thereof a predetermined shaped tip on one side of the elongated member which is spaced from the dorsal section and on the same side of the elongated central body as the curvature of the dorsum section, and an anchoring means which is preferably in the shape of a keel which is located on the elongated body under the predetermined shaped tip thereby providing sufficient additional material to provide the desired shaping, contouring and elevation of the nose and nasal tip.

Another advantage of the present invention is that the surgeon, during surgery, can trim the dorsal section, predetermined shaped tip or keel, as specifically required for the specific implantation being conducted by the surgeon, thereby providing individual contouring and profiling the nose meeting the desires of the patient.

Another advantage of the present invention is that the contour nasal implant can further include a septum strut so that the contour nasal implant can be used for both caucasian and non-caucasian implantation, depending upon the patient's desires, needs and physical structure of the nose.

Another advantage of the present invention is that the contour nasal implant can have a predetermined shaped tip that is square shaped, generally rounded or partially rounded or contoured in the form of a truncated pyramid to provide the surgeon with a wide range of predetermined shaped tip sizes to perform the desired the reshaping and elevation of the nasal tip of the nose of a patient into which the contour nasal implant is implanted.

Another advantage of the present invention is that the keel can be positioned to have its outside edge either flushed with or spaced from the outside edge of the central body member relative to the predetermined shaped tip.

Another advantage of the present invention is that the dorsal support end or dorsal section, which is formed into an arcuate shaped contoured end can have a variety of thicknesses in the contoured section to provide the surgeon with a selection of various thicknesses to control the amount of elevation of the nose relative to the nasal dorsum.

Another advantage of the present invention is that the implant can be formed of a non-biodegradable elastomeric material. In the preferred embodiment a non-biodegradable elastomeric material is selected to be silicone elastomer.

Another advantage of the present invention is that the contour nasal implant can be utilized in a novel and unique method for surgically implanting the same into the nose of a patient. The method for surgically implanting the contour nasal implant into the nose of the patient is adapted to elevate and augment the frontal and profile views of the patient's nose while permitting the surgeon to trim and otherwise prepare the contour nasal implant during the surgical process to meet the specific needs of the patient into which the same is to be implanted. The surgeon can trim any one of the dorsal sections, the predetermined shaped tip and the keel of the contour nose implant to obtain the design contour and profile for the patient into which the same is implanted.

Another advantage of the method of the present invention is that the surgeon can make a determination as to the amount of elevation required of the nose in determining the best procedure to utilize in elevating the skin relative to the nasal dorsum. If the nasal skin of the patient into which the contour nasal implant is to be implanted is thick over the nasal dorsum, the surgeon can elevate the nasal skin alone from the nasal dorsum to receive the contour nasal implant. On the other hand, if the nasal skin of the patient into which the contour nasal implant is to be implanted is thin over the nasal dorsum, the surgeon can elevate some of the soft tissue from the nasal dorsum along with the skin to provide the additional padding required between the dorsal section of the contour nasal implant and the skin.

Another advantage of the present invention is that the surgeon can utilize biodegradable suture material, such as catgut which contains collagen or a suture material containing collagen, to suture the rhinoplasty incision to provide the minimum scarring disfigurement in the vicinity of the incision and to result in reducing, to the extent reasonably possible, the appearance of the rhinoplasty incision in the nose.

Another advantage of the present invention is that the surgeon has the ability to utilize a non-biodegradable suturing material for suturing the skin to the nasal dorsum. When the nose has sufficiently healed, the non-biodegradable suturing material can be removed from the patient's nose.

BRIEF DESCRIPTION OF THE DRAWING

The foregoing and other advantages of the this invention will be apparent from the following description of the preferred embodiment of the invention when considered with the illustrations and accompanying drawings which include the following figures:

FIG. 1 is a front perspective view of a contour nasal implant showing the top, front and left end of the preferred embodiment;

FIG. 2 is a bottom perspective view of the contour nasal implant showing the bottom, rear and right end view of the preferred embodiment;

FIG. 3 is a front elevational view thereof;

FIG. 4 is a top plan view thereof;

FIG. 5 is a bottom plan view thereof;

FIG. 6 is a left side elevational view thereof;

FIG. 7 is a right side elevational view thereof; and

FIG. 8 is a front plan elevational view of a second embodiment of the invention.

FIG. 9 is a right side elevational view of the second embodiment of the invention as shown in FIG. 8;

FIG. 10 is a front plant elevational view of a third embodiment of the invention;

FIG. 11 is a right side elevational view of the third embodiment of the invention as shown in FIG. 10;

FIG. 12 is a front plan elevational view of a fourth embodiment of the invention;

FIG. 13 is a left side elevational view of the fourth embodiment of the invention as shown in FIG. 12;

FIG. 14 is a right side elevational view of the fourth embodiment of the invention as shown in FIG. 12;

DESCRIPTION OF THE PREFERRED EMBODIMENT

Figure 15:
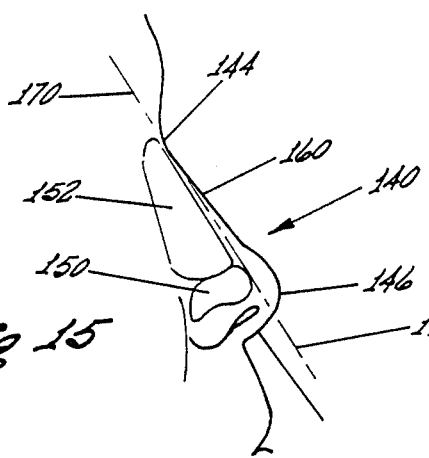
FIG. 15 is a pictorial illustration of a nose of patient, before surgery, having a line drawn thereon to connect the highest points of the superior palpebral sulci such that the line crosses the nasal dorsum at a point representing the nasion and the highest point of implantation insertion.

FIGS. 1 through 7 disclose the preferred embodiment of a contour nasal implant which is shown generally as 30. In FIGS. 1 through 7 the contour nasal implant 30 includes an elongated central member 32 having a first end shown generally as 36 and a second end shown generally as 40. The second end 40 is spaced a predetermined distance from the first end 36. As illustrated in FIGS. 1, 2 and 7, the first end 36 is flared or defines a generally concave surface comprising the dorsal support end or dorsal section 44. The dorsal support end or dorsal section 44 is formed into an arcuate shaped contoured end which is utilized to shape the frontal and profile views of the nasal dorsum of a patient into which the same is to be implanted. The second end 40, which is located in an opposed spaced relationship to the first end 36, includes means defining a tip having a predetermined shape, shown generally as 50. The predetermined shaped tip 50 is located on the same side of the elongated central member as the direction of the curvature of the dorsal support end or dorsal section 44. The second end 40 further includes anchoring means, such as for example, a keel, shown generally as 48, having a selected width and length. The keel 48 is located on the second end 40 under the predetermined shaped tip 50. The keel 48 is positioned substantially perpendicular to the elongated central member 32 with the length of the keel generally parallel to the elongated central member 32. The predetermined shaped tip 50 is operative to elevate the nasal tip of the nose of a patient into which the contour nasal implant is implanted as shown generally in FIG. 18.

The contour nasal implant of FIGS. 1 through 7 has a predetermined shaped tip which is generally trapezoidal shaped. However, it is envisioned that the predetermined shaped tip could have any number of predetermined shapes, such as for example, square shaped, generally rounded, partially rounded, or the form of a truncated pyramid. Certain of these are illustrated in connection with the discussions of FIGS. 8 through 14 hereinbelow.

In the embodiment illustrated in FIGS. 1 through 7, the keel 48 has an outside edge 52 and an inside edge 54. Also, the predetermined shaped tip 50 has an outer edge, shown generally as 56. In the embodiment of FIGS. 1 through 7, the outside edge 52 of the keel 48 is located away from the outer edge 56 of the predetermined shaped tip 50. When the contour nasal implant 30 is implanted into the nose of a patient, the keel 48 selected to be of an appropriate dimension such that the keel thereof extends downward between the lower lateral cartilages of the patient until the desired implantation position is obtained. This will be discussed further in connection with FIG. 18.

FIGS. 8 and 9 illustrate another embodiment of a contour nasal implant. The contour nasal implant of FIG. 8 has an elongated central member shown generally as 70. The predetermined shaped tip, shown as 76, is partially rounded compared to the generally rounded predetermined shaped tip 50 of FIGS. 1 through 7. Also, the elongated central member has a dorsal support end or dorsal section 78 which is substantially thicker in dimension relative to the dorsal support end or dorsal section 44 illustrated in FIGS. 1 through 7. Also, FIG. 8 illustrates that the predetermined shaped tip 76 has an outside edge 82 and that the keel 80 has an outside edge 84. In the embodiment illustrated in FIG. 8, the outside edge of the keel 80 is substantially flush with the outside edge 82 of the predetermined shaped tip.

FIGS. 10 and 11 illustrate another embodiment of a contour nasal implant shown generally as 90. The contour nasal implant 90 includes an elongated central member 92 having a predetermined shaped tip 96 located at one end thereof and a dorsal support end or dorsal section 98 located at the other end thereof. The predetermined shaped tip 96 of the contour nasal implant 90 illustrated at FIG. 10 is substantially higher in shape and is essentially formed into a truncated pyramid. Also, the thickness of the dorsal support end or dorsal section 98 is substantially thinner in dimension relative to the dorsal support end or dorsal section illustrated in FIGS. 1 through 7. Further, the predetermined shaped tip 96 includes an outside edge 102 and the keel 100 includes an outside edge 104. In the embodiment illustrated in FIG. 10, the outside edge 104 of the keel 100 is substantially flush with the outside edge 102 of the predetermined shaped tip 196.

FIGS. 1 through 11 are intended to show several possible embodiments of the contour nasal implant for practicing this invention. The surgeon can select a contour nasal implant having a selected predetermined shaped tip or a dorsal support end or a dorsal section having the desired thickness so that when the same is inserted into the nose of the patient, the desired profile and frontal views can be obtained and the desired elevation and reshaping of the nose can be obtained.

FIGS. 12, 13 and 14 illustrate yet another embodiment of a contour nasal implant for practicing the invention. In the embodiment illustrated in FIGS. 12, 13, and 14, the contour nasal implant 110 has a substantial amount of material formed therein where a substantial amount of elevation is required in both the nasal dorsum area and in the nasal tip area. The contour nasal implant 110 includes the elongated central member 112 which has a fairly high, rounded predetermined shaped tip 106 and a significantly arcuate shaped and contoured dorsal support end or dorsal section 118. In addition, the contour nasal implant includes a keel 120 which is located under the predetermined shaped tip 106. The length of the keel 120 extends substantially parallel to the elongated central member 112. The contour nasal implant 110 further includes a septum strut 122 to provide extra elevation of the nasal tip when the same is required in order to obtain a desired shape and elevation of the nasal tip. In the embodiment illustrated in FIGS. 12, 13, and 14, the predetermined shaped tip 106 has an outside edge 112 and the septum strut 122 has an outside edge 124. The outside edge 112 or the predetermined shaped tip 106 and the outside edge 124 of the septum strut are substantially flush. The wedge 120 can have its outside edge either spaced a predetermined distance in from the outside edge 112 or the predetermined shaped tip 106 in the manner illustrated in FIGS. 1 through 7 or can have its outside edge substantially flush with outside edge 112 of the predetermined shaped tip 106 in a manner similar to the illustration of keel of FIGS. 8 and 10 discussed hereinbefore.

In connection with the contour nasal implant described in connection with FIGS. 1 through 14 hereinabove, the implant is preferably fabricated with a non-biodegradable, elastomeric material. In the preferred embodiment, a non-biodegradable elastomeric material is selected to be a silicone elastomer. One example of a silicone elastomer which can be utilized in practicing this invention is a material offered for sale and sold by Dow-Corning Corporation under the tradename Silastic, identified medical grade, ETR EALST, PT A. The elastomeric material selected for practicing this invention has a durometer rating of between about 75 durometers and about 20 durometers. In the preferred embodiment, the elastomeric material is selected to be a material having a durometer rating of about 35 durometers.

Referring now to FIGS. 15 through 19, these figures generally relate to certain of the steps used for the method of surgically implanting the contour nasal implant into the nose of a patient.

In FIG. 15, the nose of the patient is shown generally as 140, and is typical of one of the type of nose of a patient for which a contour nasal implant as disclosed herein can be utilized. The nose 140 has a hanging tip 146 resulting in the nose that hangs towards the upper lip. The nose 140 includes lateral lower cartilages 150 and a nasal bone which has a nasal dorsum 152 which extends to the in superior palpebral sulci 170 shown generally by arrow 172. The nasal dorsum 152 terminates at the nasion, which is the point in the skull at which the suture between the two nasal bones meet in suture between the nasal bones and the frontal bone, and the nasion is shown generally as 144. The nasal tip 146 hangs from the lateral lower cartilages. In the embodiment illustrated in FIG. 15, the nasal dorsum and nasal tip are to be elevated and are to augment the frontal and profile views of the patient nose 140. Thus, the first step of the surgical process starts with the surgeon drawing, onto the nose of a patient into which the contour nasal implant is to be surgically implanted, a line, shown as 172, which is used to connect the highest points of the superior palpebral sulci 170, such that the line crosses the nasal dorsum 152 at a point representing the nasion 144 and the highest point of implant insertion.

Figure 16:
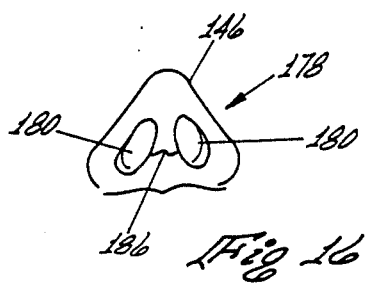
FIG. 16 is a pictorial representation of the nostrils of a patient after a rhinoplasty incision has been made between the nostrils.

Thereafter, the surgeon places two padgets in each nostril of the nose of the patient. Thereafter and as shown in FIG. 16, the surgeon then performs the step of making a rhinoplasty incision 186 into the skin located between the nostrils 180 of the patient's nose 178.

Figure 17:
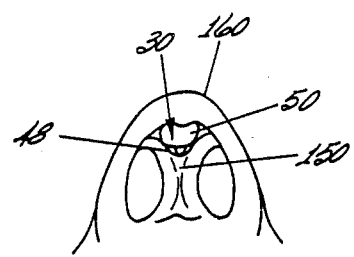
FIG. 17 is a pictorial representation of the step of the columella skin being retracted superiorly and with the skin being dissected off the dorsum of the nose to the line previously drawn across the nasal dorsum and with the contour nasal implant inserted into the nose of the patient.
Figure 18:
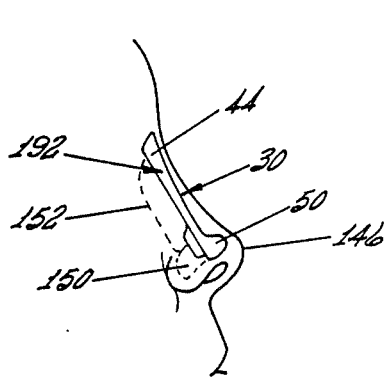
FIG. 18 is a pictorial representation of the nose of a patient after the contour nasal implant is implanted in position and before closing of the rhinoplasty incision showing elevation of the skin over the nasal dorsum and the elevation and reshaping of the nasal tip.

FIGS. 17 and 18 depict the results of the next three steps which include:

(1) retracting superiorly the columella skin off of the lower lateral cartilages 150 on each side of the nostril 180 up the highest point of the natural dome of the nose of a patient;

(2) dissecting the skin off of the nasal dorsum of the nose to the line 172 previously drawn across the nasal dorsum; and (3) implanting a contour nasal implant shown generally as 30, having an elongated central member having a first end and a second end, of which the predetermined shaped tip 50 as illustrated in FIG. 17, and the dorsal section 44 as illustrated in FIG. 18, such that the dorsal section is adapted to be positioned over the nasal dorsum 152 into the nose of a patient into which the same is implanted. The second end or dorsal section 44 includes a predetermined shaped tip located on the same side of the elongated central member as the curvature of the dorsal section and further includes a keel 48 having a selected width and length which is located under the predetermined shaped tip 50. The keel 48 has a length which is generally parallel to the elongated central member such that the dorsal section 44 is positioned between the nasal dorsum 152 and the skin 160 of the predetermined shape tip is located on the lower lateral cartilages 150. As illustrated in FIG. 17, the keel 48 extends downward between the lower lateral cartilage until the desired implantation position is obtained.

Figure 19:
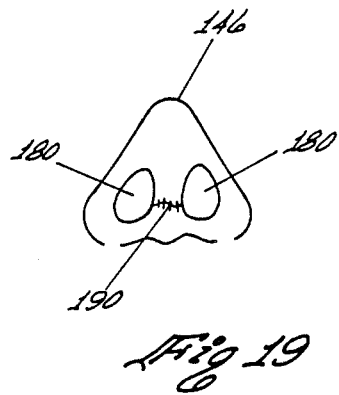
FIG. 19 is a pictorial representation of suturing the rhinoplasty incision in the skin between the nostrils with biodegradable suturing material.

As illustrated in FIG. 19, the next step is suturing the rhinoplasty incision between the nostrils 180 to implant the contour nasal implant 30 within the nose of the patient to augment the frontal and profile views of the patient and to elevate the nasal tip 146 of the nose of the patient.

The surgeon can perform a number of other ancillary steps which will include the following. The skin 160 in the area of the nasal dorsum can be sutured to the nasal dorsum 152 to ensure proper healing thereof. Preferably, the skin is sutured to the nasal dorsum by the use of a non-biodegradable suturing material.

Also, it is preferable to use a biodegradable suturing material to suture the rhinoplasty incision in the skin between the nostrils of the patient. Preferably, the biodegradable suturing material can be catgut or some other suturing material having a high percentage of collagen as a part thereof, as is well known in the trade. Typical catgut that can be utilized for practicing in this invention is that described in the Physician's Desk Reference For Ophthalmology, PDR 15th Edition, Section 3 thereof entitled "Suture Materials", pages 21 and 22.

Thereafter, the surgeon can perform the step of removing the non-biodegradable suturing material from the skin and nasal dorsum after the nose has healed, ensuring that the contour nasal implant remains in position.

During the surgical process, the surgeon can select the desired contour nasal implant having the characteristics described with respect to FIGS. 1 through 14 hereof and, during the surgery, can hold the contour nasal implant relative the nose and trim any one of or all of the dorsal sections, the predetermined shaped tip and the keel prior to implantation of the same so that the desired contour and profile for the patient into which the same is implanted can be obtained.

An example of the contour nasal implant surgery, including the steps taken by surgeons practice this invention, is set forth hereinbelow.

EXAMPLE I

The contour nasal implant is usually inserted under local anesthesia. A line is drawn with a marking pen connecting the highest points of the superior palpebral sulci. Where this line crosses the nasal dorsum represents the nasion and the highest point of implant insertion. The patient is given intravenously Versed 2.5 mg to 5 mg. Also, 1 mg of Robinul is given intravenously prior to prepping and draping. After marking, the patient is prepped with an iodinated skin antiseptic solution such as a BETADINE solution about the face while two BETADINE pledget (a compress or pad used to apply medication to or absorb discharges from a wound) are placed in each nostril. BETADINE is a trademark for iodined skin antiseptic. The generic name is povidone-iodine 7.5%. Just prior to the injection of local anesthetic 25 mg of Ketamine is administered and approximately one minute is allowed to lapse. 3 to 5 cc of 2% Xylocaine in 1:e100,000 Adrenalin are then injected into the columella, the superior rim of the nostril corresponding to the lower border of the lower lateral cartilage on each side and the remainder along the dorsum of the nose lateral to the midline so as not to obscure the nasal profile.

An open rhinoplasty incision made in the standard fashion. The columella skin is retracted superiorly, the skin is elevated carefully off the lower lateral cartilages on each side up to the highest point of the natural dome of the patient. If the patient has thin nasal skin, the soft tissue between the lower lateral cartilages is elevated with the skin to provide more padding for the implant. If the nasal skin is thick, then the skin only is elevated. Thick skin can be treated by removing the thickened undersurface of the skin scoring the skin horizontally to allow it to drape in a more favorable fashion. Care must be taken to not·thin excessively or make the relaxing incisions too deep so as to allow the implant to extrude. Sharp scissors used to complete the dissection of the skin off the dorsum of the nose to the line previously drawn across the nasal bridge. A predetermined sized contour implant has been removed and has been soaking in BETADINE Solution. The implant is removed from the solution and held over the nose to approximate its implanted position. This allows for trimming of the implant to the proper length and to the proper nasal frontal angle for each patient. This trimming is necessary in 90% of patient's. The tip of the implant should rest on the patient's lower lateral cartilages with the keel extending down between the lower lateral cartilages. Further trimming is required at the tip, usually on the sides to round off the implant where it rests on the lower lateral cartilages. The height of the newly formed tip can be adjusted by trimming the keel to the extent necessary. Once the implant is in position, it must be straight or must be trimmed accordingly. Contour can be checked by replacing the skin into its original position. Further stabilization of the implant is provided by passing a 5-0 nylon suture between the lower lateral cartilages through the keel of the implant. The skin is replaced and sutured into position with three 5-0 nylon sutures in the columella and multiple 5-0 chromic catgut sutures for the rim portion of the open rhinoplasty incision.

Dressings consist of ¼ inch Steristrips placed just posterior to the high point of the tip in a horizontal fashion and a vertical Steristrip placed from the base of the columella over the tip onto the dorsum of the nose. Preparing the skin with Mestasol aids in holding the strips for several days. Additional ½ inch tape can be placed across dorsum if there has been more bleeding than usual. The nylon sutures are removed in five days while the chromic sutures are allowed to dissolve by the twice daily application of antibiotic ointment in the nares.

Although the preferred embodiment described herein is for a non-caucasian type implantation, variations thereof can be utilized with caucasians that have a similar problem. In certain instances the separate septum strut can be utilized with the highly flared end, as illustrated in FIGS. 12, 13 and 14, where a large contouring is required for the nose. The septum strut can likewise be trimmed so that the desired shaping and elevation of the nose can be obtained.

In the form of aesthetic rhinoplasty surgery, incisions are made on the nose inside the nostril to provide access to the lateral lower cartilage and nasal dorsum or bone, so that the implant can be inserted and the desired profile and frontal views and reshaping of the nasal tip can be accommodated to meet the needs and desires of the patient. The extent of the surgery and the required steps are a function of what changes are desired by the patient and what a surgeon deems appropriate with respect to performing the various steps of surgery.

In post-operative recovery, the surgeon may find it necessary to use a splint. Also, the nasal packing may have to stay in the nose for several days before it is removed.

The goal of performing aesthetic rhinoplasty surgery is to perform as much of the surgery as possible from inside the nose so there is no visible scarring or the like. If narrowing of the flared nostrils is required, it is envisioned that some outside incisions may be required, but a surgeon skilled in the trade will perform such an incision that the scar is barely visible in the crease of each of the nostrils.

The degree of improvement desired by the patient can be achieved by utilizing the capability of the contour nasal implant to being trimmed or otherwise performed in a manner to obtain the desired elevation and reshaping of the nasal tip. The goal in performing such surgery and in the use of the contour nasal implant inside surgery is to create a "natural" look so that the surgery obtains the desired and pleasing aesthetic results, taking into the account the physiological structure of the patient's nose.

What is claimed is:

1. A method for surgically implanting a contour nasal implant into the nose of a patient wherein the nose has lateral lower cartilages, a nasal dorsum and a nasal tip wherein the nasal dorsum and nasal tip are to be elevated and augment the frontal and profile views of the patient's nose comprising the steps of
   drawing, onto the nose of a patient into which a contour nasal implant is to be surgically implanted, connecting the highest points of the superior palpebral sulci such that the line crosses the nasal dorsum at a point representing the nasion and the highest point of implant insertion;
   placing two pledgets in each nostril of the nose of said patient;
   performing an open rhinoplasty incision into the skin located between the nostrils of the patient;
   retracting superiorly the columella skin off of the lower lateral cartilages on each side of the nostril up to the highest point of the natural dome of the nose of the patient;
   dissecting the skin off of the nasal dorsum of the nose to the line previously drawn across the nasal dorsum;
   inserting a contour nasal implant having an elongated central member having a first end and a second end wherein the first end thereof has a dorsal section having a concave curvature on a selected side which is adapted to be positioned over the nasal dorsum in the nose of a patient into which the same is to be implanted and wherein the second end includes a predetermined shaped tip located on the same side of the elongated central member as the concave curvature of the dorsal section and further includes a keel having a selected width and length which is located under said predetermined shaped tip and wherein the keel has a length which is generally parallel to the elongated central member such that the first end thereof having the dorsal section is positioned between the nasal dorsum and the skin while the predetermined shaped tip is located on the lower lateral cartilages and the keel thereof extends downward between the lower lateral cartilages until the desired implantation position is obtained; and
   suturing the rhinoplasty incision in the skin between the nostrils to implant the contour nasal implant within the nose of the patient to augment the frontal and profile views of the patient and to elevate the nasal tip of the nose of a patient.

2. The method of claim 1 further comprising the step of:
   suturing the skin to the nasal dorsum.

3. The method of claim 2 wherein the step of suturing further includes suturing the skin to the nasal dorsum with a non-biodegradable suturing material.

4. The method of claim 3 further comprising the step of
   removing the non-biodegradable suturing material from the skin and nasal dorsum.

5. The method of claim 3 wherein the non-biodegradable suturing material is selected to be nylon suturing material.

6. The method of claim 1 wherein the step of suturing further includes suturing the rhinoplasty incision in the skin between the nostrils of the patient with a biodegradable suturing material.

7. The method of claim 6 wherein the biodegradable suturing material is selected to be chroma catgut material.

8. The method of claim 7 wherein the biodegradable suturing material is selected to include a collagen.

9. The method of claim 1 further comprising the step of
   trimming at least one of the dorsal section, the predetermined shaped tip and the keel of the contour nose implant to obtain a desired contour and profile of the nose of a patient into which the same is implanted.

10. The method of claim 1 further comprising the steps of
    determining if tissue padding is required to support the nasal skin; and
    if the nasal skin of the patient into which the contour nasal implant is to be implanted does not require padding to support the nasal dorsum skin, elevating the nasal skin from the nasal dorsum to receive the contour nasal implant.

11. The method of claim 1 further comprising the steps of
    determining if tissue padding is required to support the nasal skin; and if the nasal skin of the patient into which the contour nasal implant is to be implanted does require padding to support the nasal dorsum skin, elevating soft tissue from the nasal dorsum with the skin to provide additional padding between the dorsal section of the contour nasal implant and the skin.

12. The method of claim 1 further comprising the step of soaking the contour nasal implant in an iodinated skin antiseptic prior to implanting the same in the nose of the patient.

13. The method of claim 9 wherein the iodinated skin antiseptic solution is selected to be a povidone-iodine 7.5% solution.

14. The method of claim 1 wherein the pledgets are treated with an iodinated skin antiseptic solution.

15. The method of claim 1 wherein the contour nasal implant is selected to be an integrated contour nasal implant formed of an elastomeric material.

16. The method of claim 15 wherein the elastomeric material is selected to be an elastomer silicone material.

* * * * *